(12) United States Patent
Mori et al.

(10) Patent No.: US 9,646,138 B2
(45) Date of Patent: May 9, 2017

(54) BIOIMAGING GRID

(71) Applicant: The Johns Hopkins University, Baltimore, MD (US)

(72) Inventors: Susumu Mori, Ellicott City, MD (US); Michael I. Miller, Towson, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 147 days.

(21) Appl. No.: 14/367,593

(22) PCT Filed: Dec. 31, 2012

(86) PCT No.: PCT/US2012/072322
§ 371 (c)(1),
(2) Date: Jun. 20, 2014

(87) PCT Pub. No.: WO2013/102215
PCT Pub. Date: Jul. 4, 2013

(65) Prior Publication Data
US 2015/0302171 A1    Oct. 22, 2015

Related U.S. Application Data

(60) Provisional application No. 61/581,740, filed on Dec. 30, 2011.

(51) Int. Cl.
G06F 19/00    (2011.01)
G06T 7/00    (2017.01)

(52) U.S. Cl.
CPC ........ G06F 19/3443 (2013.01); G06F 19/321 (2013.01); G06T 7/0014 (2013.01);
(Continued)

(58) Field of Classification Search
None
See application file for complete search history.

(56) References Cited

U.S. PATENT DOCUMENTS

| | | | |
|---|---|---|---|
| 6,173,068 B1 * | 1/2001 | Prokoski | A61B 5/015 382/115 |
| 6,226,418 B1 * | 5/2001 | Miller | G06K 9/6206 382/131 |
| 6,611,615 B1 * | 8/2003 | Christensen | G06T 5/20 128/922 |
| 6,625,303 B1 * | 9/2003 | Young | G06T 7/004 382/132 |
| 6,633,686 B1 * | 10/2003 | Bakircioglu | G06K 9/6206 382/131 |
| 8,335,694 B2 * | 12/2012 | Reiner | G06F 3/04883 705/2 |

(Continued)

FOREIGN PATENT DOCUMENTS

| | | |
|---|---|---|
| JP | 2010-172559 A | 8/2010 |
| JP | 2011-118543 A | 6/2011 |
| WO | WO-2011/163391 A2 | 12/2011 |

OTHER PUBLICATIONS

International Search Report and Written Opinion of PCT/US2012/0722322.

*Primary Examiner* — Tsung-Yin Tsai
(74) *Attorney, Agent, or Firm* — Venable LLP; Henry J. Daley; Trent B. Ostler

(57) ABSTRACT

A method may include standardizing an input image to produce a standardized input image; structurizing the standardized input image to be characterized by a plurality of anatomical properties; mapping the input image to one or more reference cases of a plurality of reference cases using the plurality of anatomical properties, wherein the one or more reference cases are associated with first non-image clinical information; and determining second non-image clinical information for the input image based on the one or more reference cases and the first non-image clinical information.

32 Claims, 9 Drawing Sheets

(52) U.S. Cl.
    CPC ........... *G06T 2207/10072* (2013.01); *G06T 2207/20128* (2013.01); *G06T 2207/30016* (2013.01)

(56) References Cited

U.S. PATENT DOCUMENTS

| | | | | |
|---|---|---|---|---|
| 2006/0233430 | A1* | 10/2006 | Kimura | G06T 7/0024 382/128 |
| 2007/0239694 | A1* | 10/2007 | Singh | G06F 17/30958 |
| 2010/0080432 | A1* | 4/2010 | Lilja | G06T 7/0012 382/131 |
| 2010/0260396 | A1* | 10/2010 | Brandt | G06K 9/4671 382/131 |
| 2010/0303318 | A1 | 12/2010 | Benali et al. | |
| 2010/0329529 | A1* | 12/2010 | Feldman | G06K 9/6252 382/131 |
| 2011/0022622 | A1 | 1/2011 | Boroczky et al. | |
| 2011/0160543 | A1* | 6/2011 | Parsey | A61B 5/055 600/300 |
| 2011/0173189 | A1* | 7/2011 | Singh | G06F 17/30958 707/722 |
| 2013/0102877 | A1* | 4/2013 | Mori | A61B 5/055 600/410 |
| 2014/0341471 | A1* | 11/2014 | Ono | A61B 5/055 382/173 |

\* cited by examiner

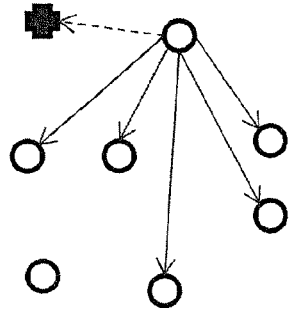
FIG. 1B: Study-specific atlas
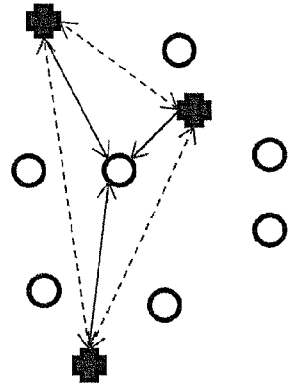
FIG. 1D: Multi-atlas (parcellation only)
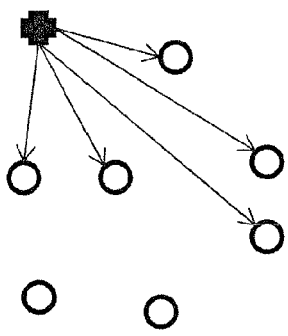
FIG. 1A: reference atlas
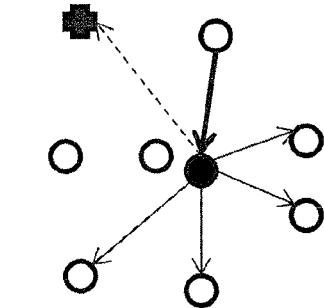
FIG. 1C: Population-averaged atlas

BIOIMAGING GRID

CROSS REFERENCE TO RELATED APPLICATIONS

This is a national stage application under 35 U.S.C. §371 of PCT/US2012/072322 filed Dec. 31, 2012, the entire contents of which are incorporated herein by reference and this application claims priority to U.S. Provisional Patent Application Ser. No. 61/581,740, the entire contents of which are hereby incorporated herein by reference.

This invention was made with Government support of Grant No. RO1AG020012 and P41 EB015909, awarded by the National Institutes of Health/DHHS. The U.S. Government has certain rights in this invention.

FIELD

Various embodiments may be generally directed to quantitative image analysis. Some embodiments may be particularly directed to methods, systems, and media for quantitative image analysis.

BACKGROUND

While the quantitative analyses based on tissue segmentation and image matching have been successfully used for brain research, none of them are routinely used for daily clinical diagnosis or prognosis. We believe that one of the fundamental reasons is the concept of the population averaging and anatomical characterization based on single atlas is not compatible with the clinical diagnosis, in which anatomical variability is inherently huge. This makes a notion of "population representative atlas" less meaningful and accuracy of image matching based on a single atlas compromised. The multi-atlas approach could be more robust in terms of registration accuracy. However, this technique has been developed to achieve better accuracy for image parcellation, which requires many pre-parcellated images. If the anatomical variability of the target population, in this case clinical populations, is large, the number of pre-parcellated atlases also needs to be large, which would pose practical problems; how to generate so many atlases with accurate pre-parcellation, which often requires manual delineations.

What would be a more fundamental problem for all the segmentation/parcellation and image-mapping approaches is, the final outcomes are mere quantitative characterization of anatomy, which does not directly provide clinically meaningful information; for example, the volume of hippocampus per se is not clinically useful. Everybody has different hippocampal volumes. There are functionally healthy elderly people with a small hippocampus volume at only 5% percentile while an Alzheimer's disease patient could have a 20 percentile hippocampus volume.

SUMMARY

Various embodiments are generally directed to evidence-based statistical diagnosis support.

One embodiment includes method for evidence-based statistical diagnosis support comprising: standardizing an input image to produce a standardized input image; structurizing the standardized input image to be characterized by a plurality of anatomical properties; mapping the input image to one or more reference cases of a plurality of reference cases using the plurality of anatomical properties, wherein the one or more reference cases are associated with first non-image clinical information; and determining second non-image clinical information for the input image based on the one or more reference cases and the first non-image clinical information.

One embodiment includes a system for evidence-based statistical diagnosis support comprising: a memory; and a processor connected to the memory and configured to: standardize an input image to produce a standardized input image; structurize the standardized input image to be characterized by a plurality of anatomical properties; map the input image to one or more reference cases of a plurality of reference cases using the plurality of anatomical properties, wherein the one or more reference cases are associated with first non-image clinical information; and determine second non-image clinical information for the input image based on the one or more reference cases and the first non-image clinical information.

One embodiment includes a computer readable storage medium for evidence-based statistical diagnosis support, the computer readable storage medium comprising instructions that if executed enable a computing system to: standardize a plurality of clinical images to produce a plurality of standardized clinical images; structurize the plurality of standardized clinical images to be characterized by a plurality of anatomical properties for each image of the plurality of standardized clinical images; create a plurality of reference cases using the plurality of anatomical properties, wherein the plurality of reference cases are associated with first non-image clinical information; and store the plurality of reference cases in a database.

One embodiment includes a method to map anatomical features of a patient of interest with respect to population data in an image-based clinical database comprising: performing unsupervised analysis using structured anatomical information or transformation matrices; and performing supervised analysis, wherein clinical information in the image-based clinical database is incorporated.

One embodiment includes a method to cluster or create hierarchy within the image data stored in a clinical database comprising: performing image mapping among pairs of data within the database; performing image structurization using image-vector or image-matrix conversion methods to produce image feature vectors or image feature matrices; and based on the image feature vectors or image feature matrices, calculating a plurality of clusters based on similarity among the image feature vectors or image feature matrices.

One embodiment includes a method to perform brain mapping and image parcellation using an iterative approach comprising: performing initial mapping or parcellation using a single-reference mapping; using a transformation matrix or structurized anatomical feature matrices to search similar references; using the cluster representative cases to further enhance the efficiency of the reference search; performing single-reference or multiple-reference image mapping or parcellation to enhance the mapping or parcellation accuracy and to produce improved mapping or parcellation information; using the improved mapping or parcellation information to search references; if necessary, further searching inside the proper clusters to obtain single or multiple references with similar anatomical features; and iteratively searching by descending the cluster hierarchy to improve the mapping and parcellation accuracy.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

Embodiments will now be described in connection with the associated drawings, in which:

FIGS. 1A-1D depict exemplary atlases in accordance with one or more embodiments.

DETAILED DESCRIPTION OF THE DRAWINGS

Exemplary embodiments are discussed in detail below. While specific exemplary embodiments are discussed, it should be understood that this is done for illustration purposes only. In describing and illustrating the exemplary embodiments, specific terminology is employed for the sake of clarity. However, the embodiments are not intended to be limited to the specific terminology so selected. A person skilled in the relevant art will recognize that other components and configurations may be used without parting from the spirit and scope of the embodiments. It is to be understood that each specific element includes all technical equivalents that operate in a similar manner to accomplish a similar purpose. The examples and embodiments described herein are non-limiting examples.

The concept of Biological Imaging Grid (BIG) provides an entirely new framework to evaluate anatomical phenotypes quantitatively and in a more clinically relevant manner.

For image analysis to provide clinically useful information, we have to realize that the image quantification (such as segmentation, parcellation, and voxel-based analyses) is merely an intermediate form of information, which would help to interpret the patient pathology more systematically and eventually improve diagnosis accuracy, precision and/or efficiency. In Biological Imaging Grid, how radiologists relate visual anatomical clues directly to diagnosis is simulated by incorporating past experience (e.g, by using an internal image database) and image similarity search into one theoretical framework.

Figure 2:
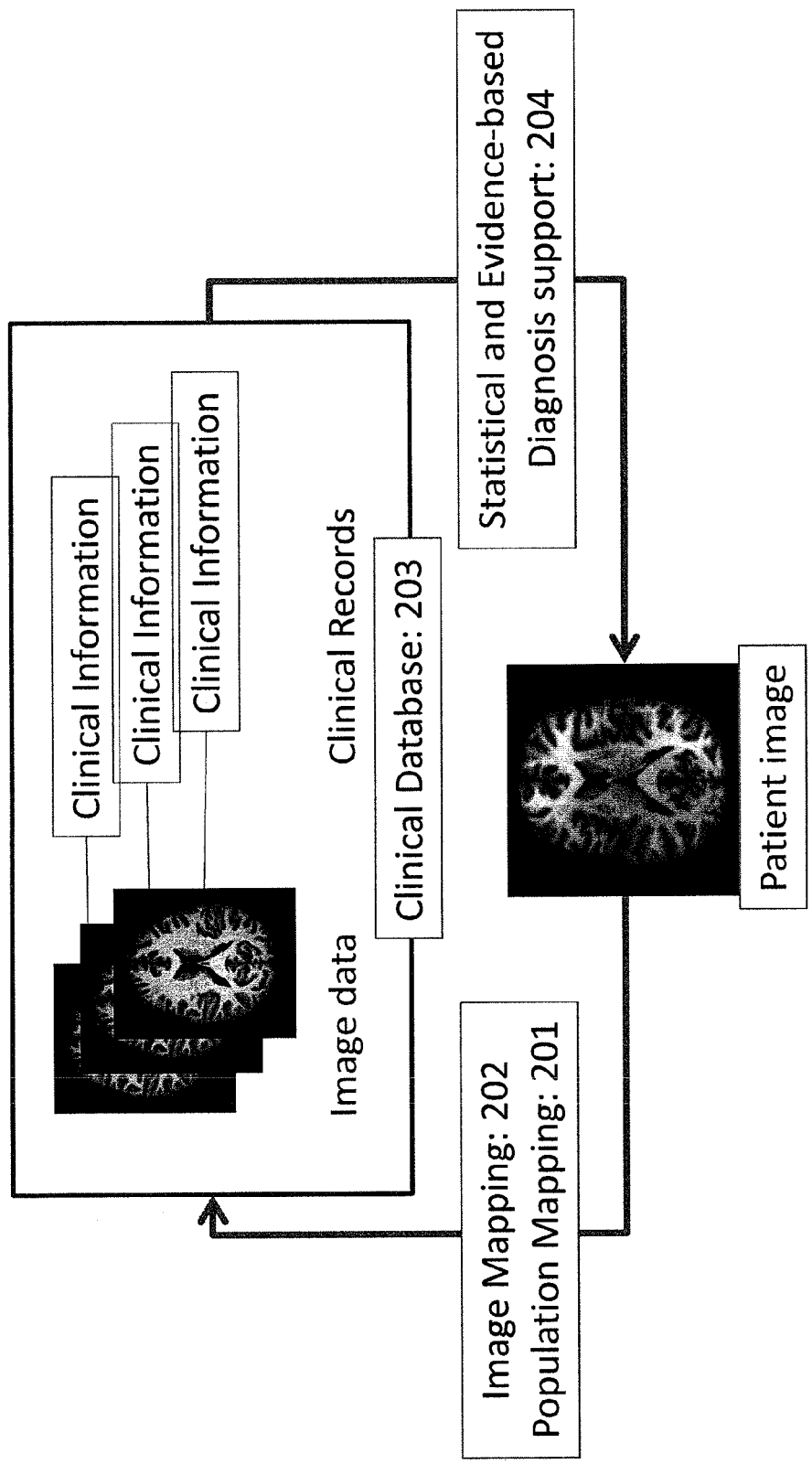
FIG. 2 depicts an exemplary biological imaging grid in accordance with one or more embodiments.

FIG. 2 depicts an exemplary biological imaging grid in accordance with one or more embodiments. The Biological Imaging grid may comprise a structured clinical database 203, two types of mapping technologies, e.g. population mapping technology 201 and image mapping technology 202, and a diagnostic support engine 204.

Figure 3:
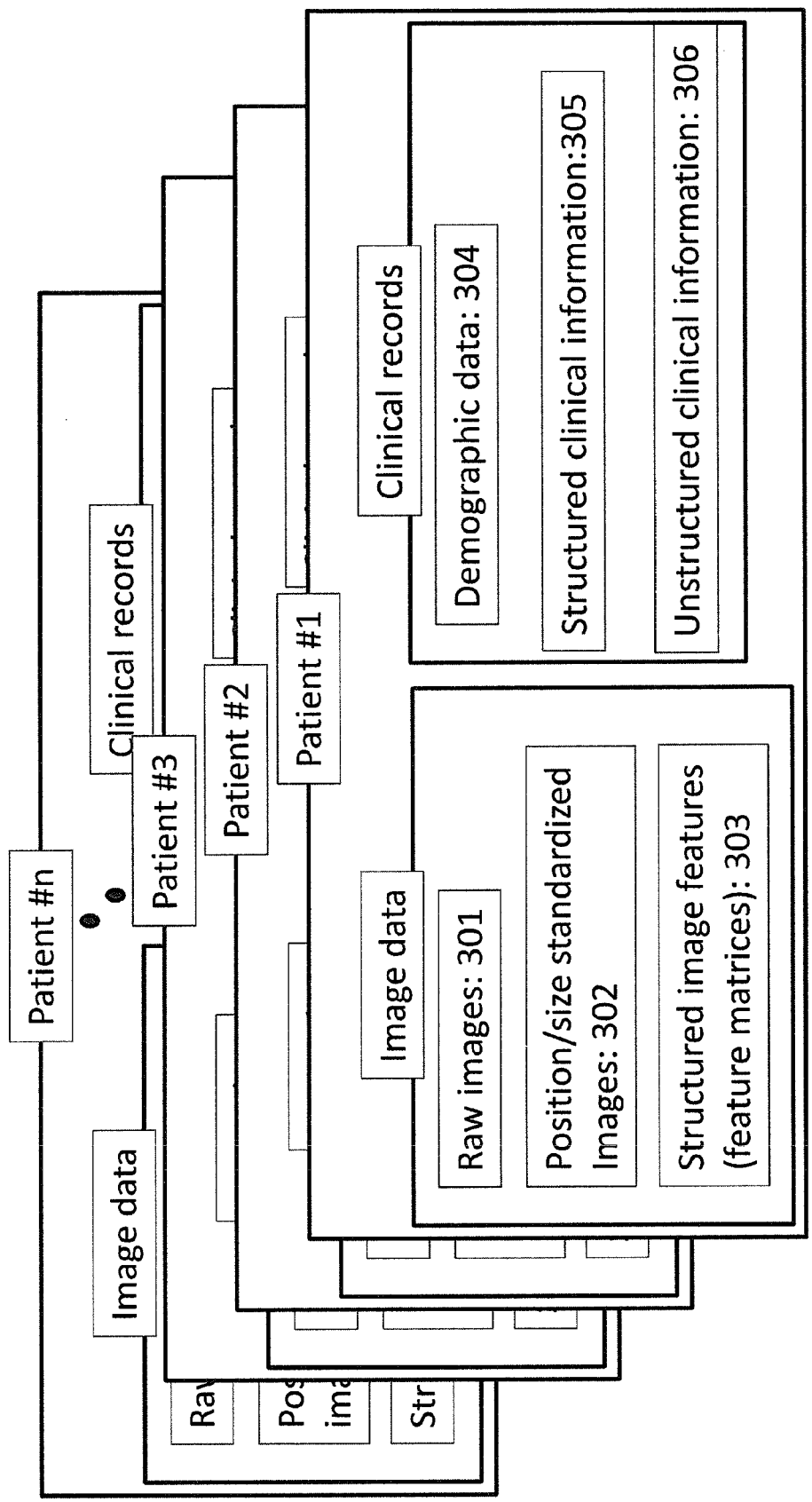
FIG. 3 depicts exemplary database entries in accordance with one or more embodiments.

FIG. 3 depicts exemplary database entries in accordance with one or more embodiments. The exemplary database entries may be stored in structured clinical database 203. Structured clinical database may store one or more entries for one or more patients or subjects. Database entries may comprise two fields for image data and clinical information of the patients. The image data will contain raw image data 301 from scanners such as MRI, CT, and PET. These raw images may be modified to align their positions and orientations, as well as the size to one or more reference coordinate systems, and stored as position/size standardized images 302. This will ensure that all image data in the database are in similar anatomical locations. The images may be further processed and converted to structured data and stored as structured image features 303 such as vectors or matrices that capture the anatomical features, which may be referred to as anatomical feature vectors/matrices. An entry may include text fields containing demographic data 304 and clinical information that is structured 305 or unstructured 306, such as free-text description.

The conversion of the images to structured image features 303 can be, for example, achieved by segmenting various structures, which converts the image data into a matrix that consists of the name of segmented structures and their volumes and signal intensities. For example, suppose a 3D MRI of a brain has dimensions of 256×256×100. If there are multiple contrasts, such as T1 and T2-weighted images, the entire data would be 2×256×256×100. If 100 structures are defined in the 3D volume data, the 3D data with 256×256× 100 data dimensions would be reduced to 100 and the total data amount become 2×200. These converted (2×256×256× 100→2×100) data are "structured" because direct comparison among subjects are possible; namely they are quantitative and standardized. Such segmentation can be achieved by the single-atlas or multi-atlas parcellation. The structured data could also be transformation matrix from or to a reference atlas or multiple atlases. The transformation matrix could be a simple 4×4 linear transformation matrix or a vector field (e.g. 3×256×256×100), in which each coordinates contains a vector indicating corresponding voxels between the two images.

Image mapping 202 may include mapping the images from a patient of interest to the existing images in the database, such as raw image data 301, position/size standardized images 302, and structured image features 303. The mapping could be image-to-image voxel-based mapping using an image transformation tool. Alternatively, the patient image may be segmented and converted to an anatomical feature matrix, followed by matrix-to-matrix comparison. After the image-to-image voxel-based mapping, the structural definition in the clinical database stored as structured image features 303 can be transferred to the patient image, achieving an atlas-based parcellation. As described above, better parcellation (structural definition) accuracy may be expected if the anatomy of the existing data in the Clinical database is similar to that of the patient of interest. Thus, a varying degree of the parcellation accuracy is expected. The level of accuracy may be estimated by monitoring the residual mapping errors (or the value of the cost function) used for the brain mapping. To speed up this process, the initial image parcellation of the patient of interest could be performed by a single-atlas-based parcellation using a common atlas depicted in FIG. 1A, converting the raw patient image into an anatomical feature matrix and existing cases inside the Clinical database that share similar anatomical phenotypes can be quickly searched, and performing multiple-atlas parcellation using the searched cases with similar anatomy.

Figure 4:
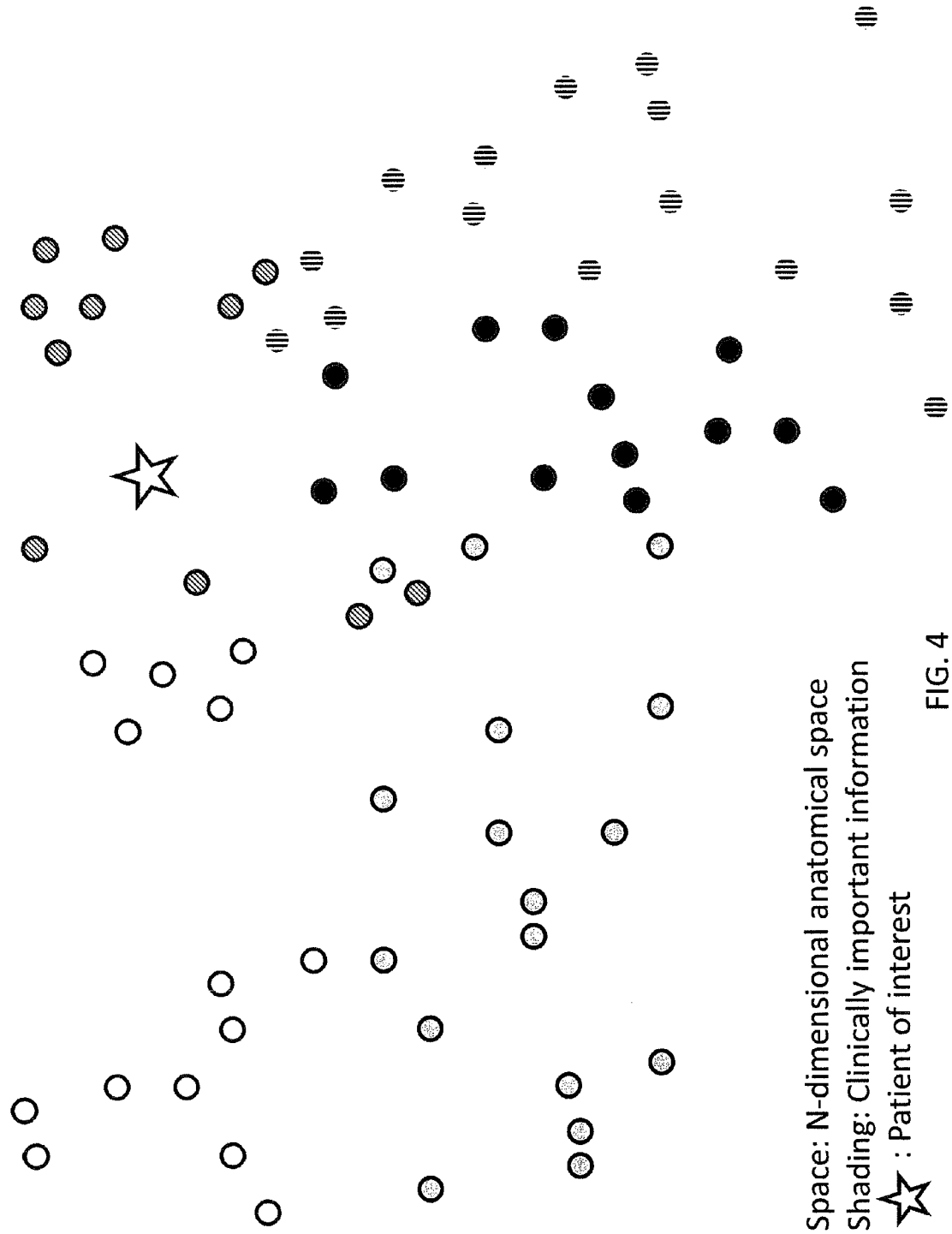
FIG. 4 depicts an exemplary N-dimensional anatomical space in accordance with one or more embodiments.
Figure 5:
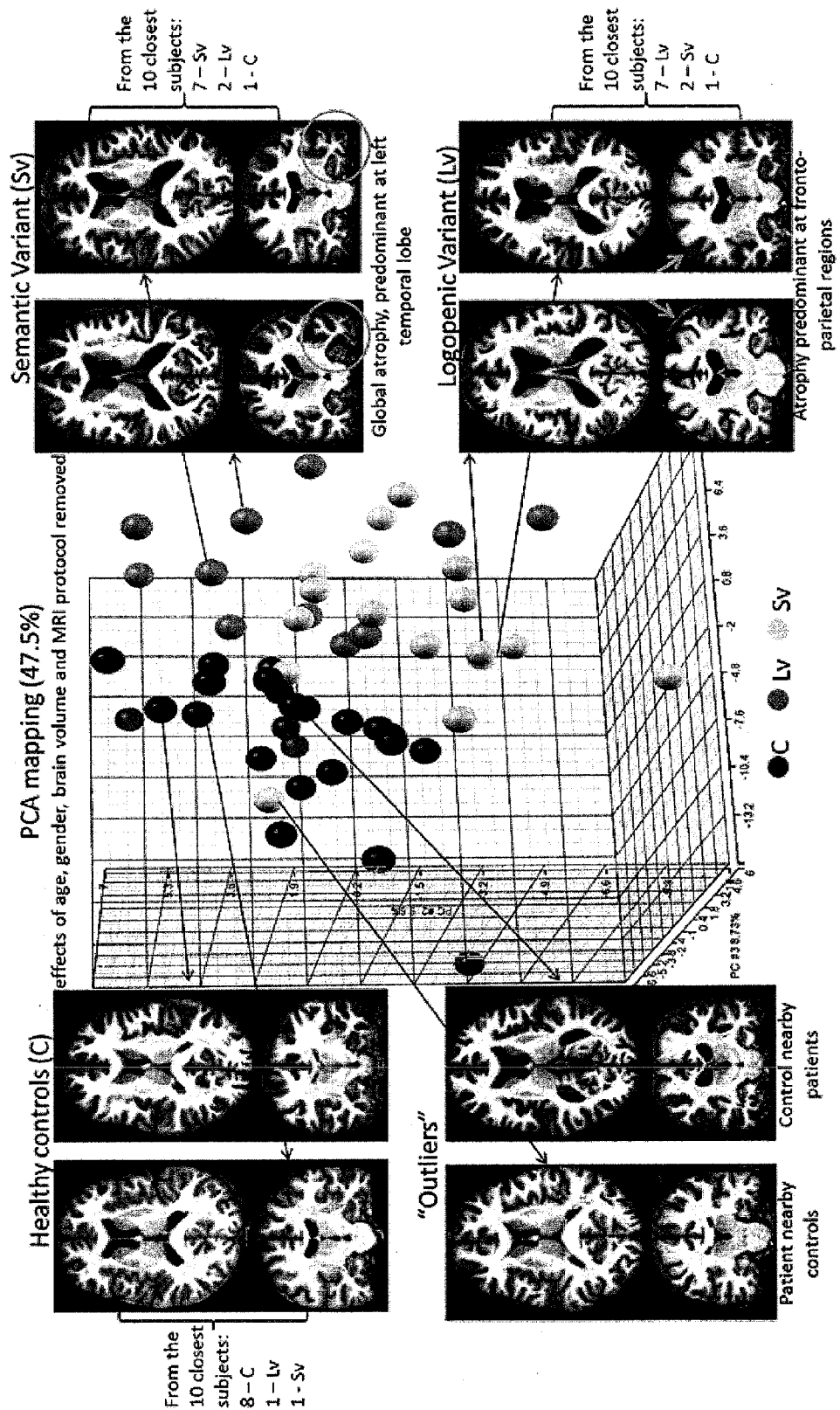
FIG. 5 depicts an exemplary mapping of anatomical similarity in accordance with one or more embodiments.

Once the image mapping 202 from a patient of interest to existing cases in Clinical database 203 is completed, the population mapping 201 may be performed. FIG. 4 depicts an exemplary N-dimensional anatomical space in accordance with one or more embodiments In FIG. 4, the space represents anatomical differences, which may be quantitatively described by the images 301 and 302 and structured data 303. For example, one of the conceptually easiest interpretations is to plot the patient anatomy in a 2D space using the whole brain volume (X-axis) and the ventricle volumes (Y-axis). In practice, the anatomical dimensions could be much larger. For example, if the brains are segmented into N structures, the anatomical space is as large as N dimensions. This dimension can be reduced by, for example, a principal component analysis (PCA), which tries to extract independent components within the N-dimension anatomical space. After the anatomical variability of M subjects is plotted in the N-dimension anatomical space, the clinical information can be associated with the anatomical space. The clinical information could be as simple as patient ages or their diagnosis information. For a patient of interest, population mapping 201 to one, more, or all of the existing patient data in the Clinical Database 203. Based on the image mapping results (including image parcellation), anatomical similarity between the patient of interest and all the patients may be estimated. FIG. 5 depicts an exemplary mapping of anatomical similarity in accordance with one or more embodiments In FIG. 5, the patient data are associated with the population data based on the distances in the PCA space.

Once the population mapping 201 is completed, the final step is to relate the patient anatomy to the population-based clinical information. In FIGS. 4 and 5, the probability of the diagnosis is estimated based on the existing patient data that share the similar anatomical features. Although the distances in the PCA space were used in the actual example in FIG. 5, the anatomical space can be created by using other types of machine learning algorithms such as linear discriminant analysis, which incorporate the clinical information to classify the anatomical features in the Clinical database.

Figure 6:
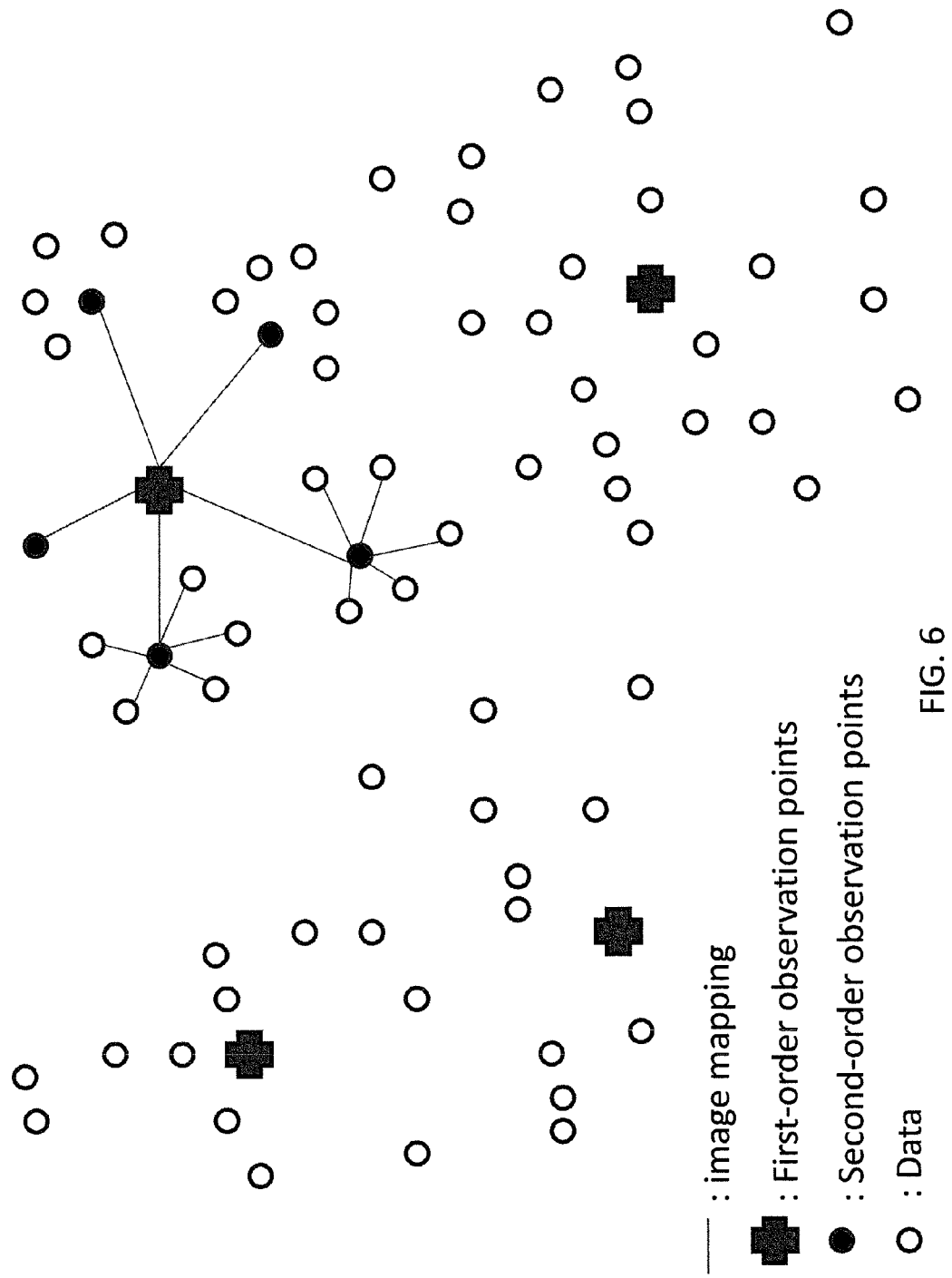
FIG. 6 depicts an exemplary N-dimensional anatomical space in accordance with one or more embodiments.

The anatomical space in FIGS. 4 and 5 can be further elaborated as shown in FIG. 6. In the above example, the image matching using population mapping 201 was performed between the patient of interest and all data in the Clinical database, which could be tens of thousands of images. The speed of this process can be enhanced by pre-populating the anatomical space. The efficiency is increased by the fact that imaging mapping between the patient of interest and those in the Clinical database with markedly different anatomical features are not necessary. Based on the image feature matrices of the patient data in the Clinical database, the patient data can be clustered and the anatomical hierarchy can be established, from which representative cases that represent the local anatomical space are chosen. The accuracy of image matching and anatomical feature matrices can be improved by performing multi-atlas parcellation within the local clusters. When the anatomy of a new patient of interest is analyzed, the initial image mapping is performed only between the patient and local representative cases (1st-order observation posts in FIG. 6). The one or multiple observation posts are selected based on the image mapping and anatomical similarity analysis. Then the detailed population mapping may be performed only within the local posts.

Figure 7:
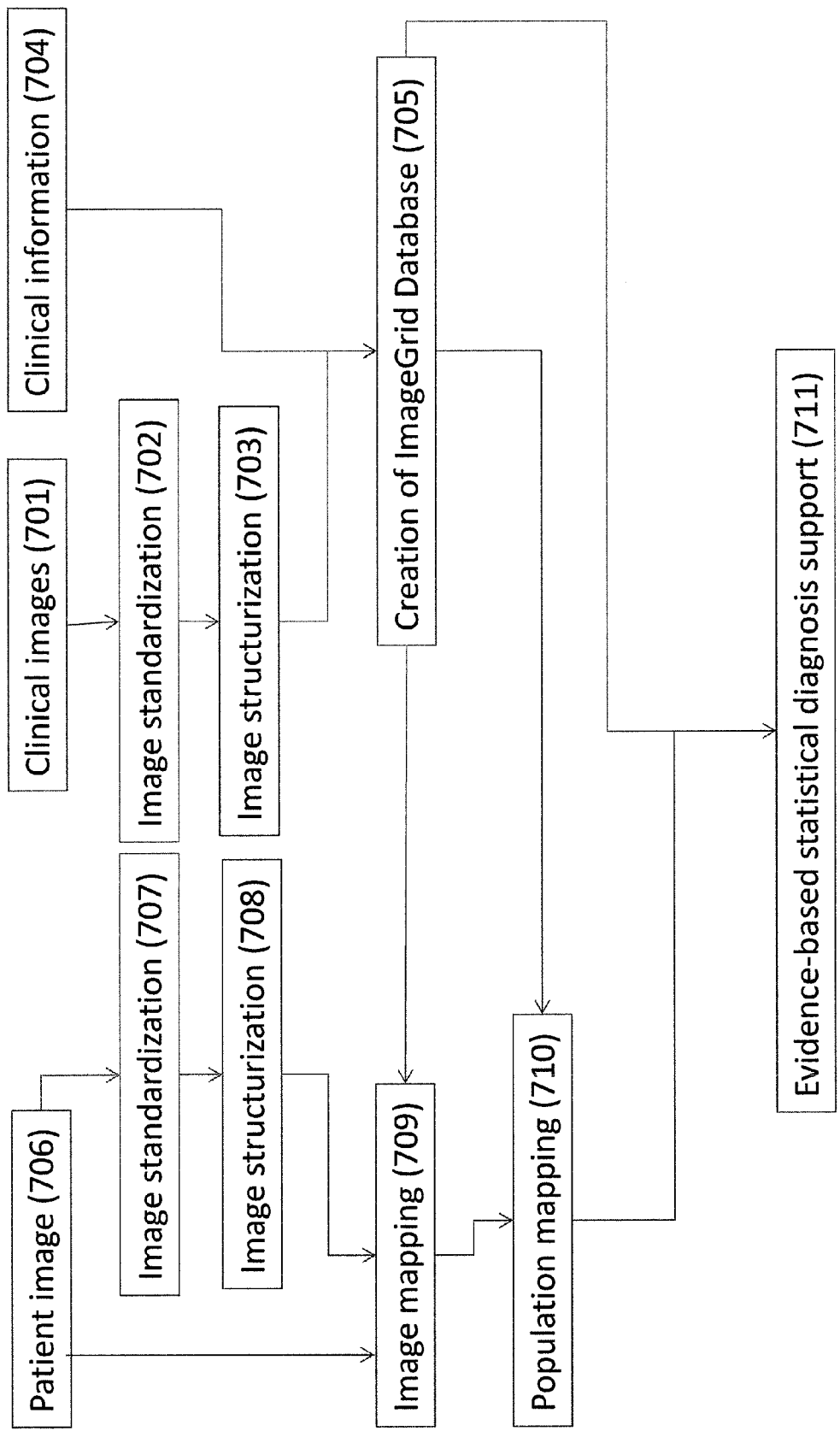
FIG. 7 depicts a block diagram of an exemplary workflow in accordance with one or more embodiments.

FIG. 7 depicts a block diagram of an exemplary workflow in accordance with one or more embodiments. A large amount of clinical data such as MRI, PET, and CT may be used as a part of the Clinical database in block 701. The images are first standardized in block 702 for their positions, orientations, and, if needed, sizes. Then the images are converted to anatomical feature matrices that capture the anatomical features in a standardized and quantitative manner, which is called "structurization" in block 703. The non-image clinical data such as gender, age, functional states, and diagnosis are incorporated to the Clinical database in block 704. For example, the anatomical data (images) can be considered as independent variables and non-image clinical data are dependent variables.

The patient images in block 706 could be standardized in block 707 and/or structurized in block 708. The patient images are then mapped to the images in the database in block 709. Using examples in FIG. 5, mapping may use the measurements of anatomical similarities (or distances in FIG. 5) from the patients to all data in the database, based on the structured anatomical information (N-dimension anatomical space). To facilitate the efficiency, the image data in the Clinical Database could be pre-clusterized and the mapping could be performed between the patient images and representative cases of the clusters. The structurization based on image parcellation can be performed using the representative atlases as multiple atlases, which are pre-parcellated.

Based on the image mapping results, the anatomical feature of each patient will be mapped to the population data in the Clinical Database in block 710. This means, past cases with similar anatomical features to the patient are identified. This procedure can be also considered as "image search", in which past cases with similar anatomical features are identified. This can be performed by identifying past cases with "short" anatomical distances, while the anatomical space may be generate by such methods as principal component analysis or linear discriminant analysis based on the N-dimension anatomical features. Then a report of the clinical information can be generated in block 711. The report could be, for example, 70% of the past cases with the similar anatomical features were diagnosed as Alzheimer's disease, the patient brain anatomy possesses anatomical features common to Huntington diseases with 80% probability, or 65% of the patients with the particular anatomical features in the patient developed language disability within 3 years. The final outcomes of BIG are this type of clinically relevant information and quantitative image analysis is an intermediate process to find past clinical cases that share clinically important anatomical features.

Figure 8:
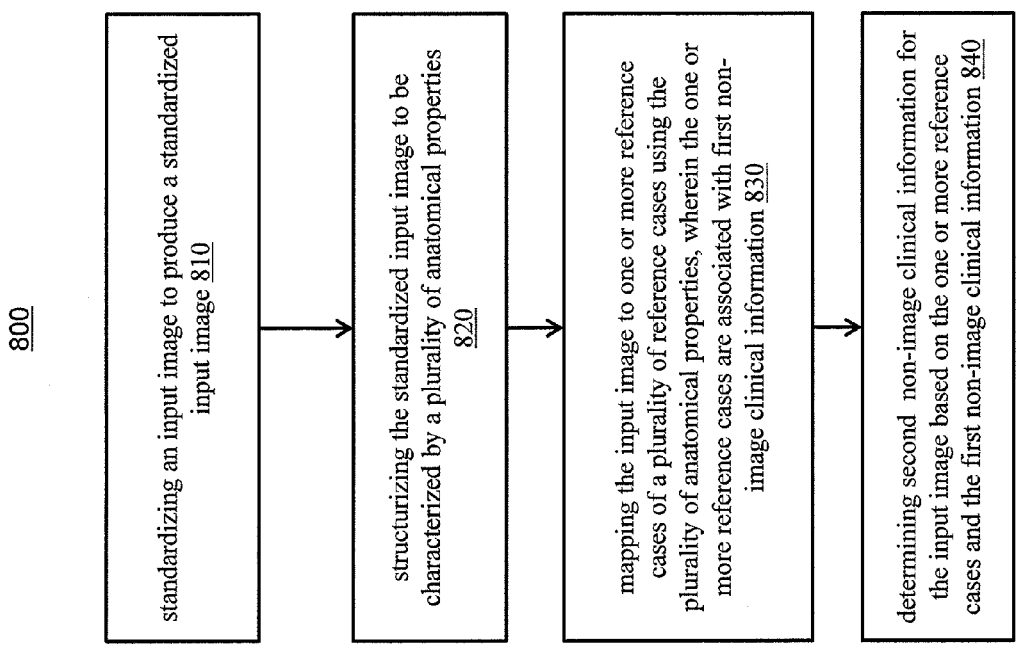
FIG. 8 depicts a block diagram of an exemplary method in accordance with one or more embodiments.

FIG. 8 depicts a block diagram of an exemplary method in accordance with one or more embodiments. In block 810, an input image may be standardized to produce a standardized input image. In block 820, the standardized input image may be structurized to be characterized by a plurality of anatomical properties. In block 830, the input image may be mapped to one or more reference cases of a plurality of reference cases using the plurality of anatomical properties, wherein the one or more reference cases are associated with first non-image clinical information. In block 840, second non-image clinical information for the input image may be determined based on the one or more reference cases and the first non-image clinical information. Any of the method steps may be performed by, using, or with a processor, computing device, part of a computing device, or any combination thereof.

In some embodiments, the one or more reference cases of the plurality of reference cases may further comprise at least one of a first order observation and a second order observation, and mapping the input image to the one or more reference cases of the plurality of reference cases using the plurality of anatomical properties may further comprises mapping the input image to at least one of the first order observation and the second order observation.

In some embodiments, the one or more reference cases of the plurality of reference cases and the input image may correspond to a same bodily segment.

In some embodiments, determining second non-image clinical information for the input image based on the one or more reference cases and the first non-image clinical information may further comprise identifying first non-image clinical information that corresponds to the one or more reference cases of the plurality of reference cases; and selecting the second non-image clinical information from the first non-image clinical information when an amount of the second non-image clinical information exceeds a threshold.

In some embodiments, the anatomical properties may be represented using one or more vectors or one or more matrices.

In some embodiments, first non-image clinical information comprises at least one of demographic information, one or more clinical symptoms, one or more functional test results, one or more diagnoses, and one or more prognoses.

In some embodiments, the second non-image clinical information may be presented as a report or transmitted to a recipient.

In some embodiments, the anatomical mapping may be based on diffeomorphic image transformation.

In some embodiments, a system for evidence-based statistical diagnosis support may comprise a memory and a processor connected to the memory and configured to: standardize an input image to produce a standardized input image; structurize the standardized input image to be characterized by a plurality of anatomical properties; map the input image to one or more reference cases of a plurality of reference cases using the plurality of anatomical properties, wherein the one or more reference cases are associated with first non-image clinical information; and determine second non-image clinical information for the input image based on the one or more reference cases and the first non-image clinical information.

In some embodiments, the one or more reference cases of the plurality of reference cases further comprise at least one of a first order observation and a second order observation, and the processor is further configured to map the input image to at least one of the first order observation and the second order observation.

In some embodiments, the one or more reference cases of the plurality of reference cases and the input image correspond to a same bodily segment.

In some embodiments, the processor is further configured to identify first non-image clinical information that corresponds to the one or more reference cases of the plurality of reference cases; and select the second non-image clinical information from the first non-image clinical information when an amount of the second non-image clinical information exceeds a threshold.

In some embodiments, the anatomical properties are represented using one or more vectors or one or more matrices.

In some embodiments, the first non-image clinical information comprises at least one of demographic information, one or more clinical symptoms, one or more functional test results, one or more diagnoses, and one or more prognoses.

In some embodiments, the processor is further configured to present the second non-image clinical information as a report; or transmit the second non-image clinical information to a recipient.

In some embodiments, a computer readable storage medium for evidence-based statistical diagnosis support may comprise instructions that if executed enable a computing system to: standardize a plurality of clinical images to produce a plurality of standardized clinical images; structurize the plurality of standardized clinical images to be characterized by a plurality of anatomical properties for each image of the plurality of standardized clinical images; create a plurality of reference cases using the plurality of anatomical properties, wherein the plurality of reference cases are associated with first non-image clinical information; and store the plurality of reference cases in a database.

In some embodiments, the computer readable storage medium may further comprise instructions that if executed enable the computing system to: standardize an input image to produce a standardized input image; structurize the standardized input image to be characterized by a second plurality of anatomical properties; map the input image to one or more reference cases of the plurality of reference cases using the second plurality of anatomical properties; and determine second non-image clinical information for the input image based on the one or more reference cases and the first non-image clinical information.

In some embodiments, the one or more reference cases of the plurality of reference cases further comprise at least one of a first order observation and a second order observation, and mapping the input image to the one or more reference cases of the plurality of reference cases using the second plurality of anatomical properties further comprises instructions that if executed enable the computing system to: map the input image to at least one of the first order observation and the second order observation.

In some embodiments, the one or more reference cases of the plurality of reference cases and the input image correspond to a same bodily segment.

In some embodiments, determining second non-image clinical information for the input image based on the one or more reference cases and the first non-image clinical information further comprises instructions that if executed enable the computing system to: identifying non-image clinical information that corresponds to the one or more reference cases of the plurality of reference cases; and selecting the second non-image clinical information from the first non-image clinical information when an amount of the second non-image clinical information exceeds a threshold.

In some embodiments, the anatomical properties are represented using one or more vectors or one or more matrices.

In some embodiments, non-image clinical information comprises at least one of demographic information, one or more clinical symptoms, one or more functional test results, one or more diagnoses, and one or more prognoses.

In some embodiments, the computer readable storage medium may further comprise instructions that if executed enable the computing system to: present the second non-image clinical information as a report, transmit the second non-image clinical information to a recipient, or any combination thereof.

In some embodiments, a method to map anatomical features of a patient of interest with respect to population data in an image-based clinical database may comprise: performing unsupervised analysis using structured anatomical information or transformation matrices; and performing supervised analysis, wherein clinical information in the image-based clinical database is incorporated. In some embodiments, an anatomy of the patient is mapped within a population based on anatomical similarity or similarity in clinically meaningful anatomical features using similarity indices.

In some embodiments, a method to cluster or create hierarchy within the image data stored in a clinical database may comprises: performing image mapping among pairs of data within the database; performing image structurization using image-vector or image-matrix conversion methods to produce image feature vectors or image feature matrices; and based on the image feature vectors or image feature matrices, calculating a plurality of clusters based on similarity among the image feature vectors or image feature matrices. In some embodiments, a representing case for each cluster is randomly selected within the cluster or calculated using population-averaging tools based on linear or non-linear image transformation.

In some embodiments, a method to perform brain mapping and image parcellation using an iterative approach may comprise: performing initial mapping or parcellation using a single-reference mapping; using a transformation matrix or structurized anatomical feature matrices to search similar references; using the cluster representative cases to further enhance the efficiency of the reference search; performing single-reference or multiple-reference image mapping or parcellation to enhance the mapping or parcellation accuracy and to produce improved mapping or parcellation information; using the improved mapping or parcellation information to search references; if necessary, further searching inside the proper clusters to obtain single or multiple references with similar anatomical features; and iteratively searching by descending the cluster hierarchy to improve the mapping and parcellation accuracy. In some embodiments, the iterative descending of a cluster hierarchy achieves improved accuracy for the population mapping by identifying similar anatomical features.

In some embodiments, an image-based clinical database is created, which will allow users to extract clinically relevant information based on anatomical features of patients. The image-based clinical database may be created by standardizing the location, orientation, and/or size of the organ of the interest; structurizing the image data by converting the anatomical information in the image to one or multiple vectors or matrices; and associating non-image clinical information, which is structurized or non-structurized, to the image data. The image structurization may include transformation fields after voxel-to-voxel image mapping, image segmentation, and single-atlas or multi-atlas-based image parcellation. The image structurization may include conversion of the image to one or multiple vectors or matrices by defining multiple structural units within the organ of interest and measure properties of each unit such as the volume and pixel intensity. The single or multiple atlases may be the images within the image-based clinical database. The non-image clinical information may include information such as demography, clinical symptoms, functional test results, diagnosis, and prognosis.

In some embodiments, patient image data may be processed to facilitate the comparison with the data in the image-based clinical database. The patient image data may be processed by standardizing the location, orientation, and/or size of the organ of the interest; and structurizing the image data by converting the anatomical information in the image to one or multiple vectors or matrices. The image structurization may transformation fields after voxel-to-voxel image mapping, image segmentation, and single-atlas or multi-atlas-based image parcellation. The image structurization may include conversion of the image to one or multiple vectors or matrices by defining multiple structural units within the organ of interest and measure properties of each unit such as the volume and pixel intensity. The formats of such vectors and matrices may be consistent with those in the clinical database to ensure the efficiency and accuracy of the comparison. The single or multiple atlases may be the images within the image-based clinical database. The parcellation accuracy may be maximized by choosing appropriate existing cases within the image-based clinical database as atlases. The appropriate atlases may be selected by anatomical similarity between the patient of interest and the cases in the database.

In some embodiments, patient image data may be mapped to the existing data in the image-based clinical database. Patient image data may be mapped by transforming the patient image to the existing data in the image-based clinical database or, conversely, transforming the existing data to the patient image; and comparing the structured image data from the patient of interest and existing data. The anatomical similarity or differences may be characterized in a standardized and quantitative way, which may include calculating transformation matrix after voxel-to-voxel image mapping; and calculating a similarity measure based on the structurized information. The accuracy of atlas-based image segmentation and parcellation, as well as the image structurization accuracy, may be improved by choosing one or multiple images in the existing database that share similar anatomical features, which may include the steps of, but not limited to, measuring similarity based on intensity differences or correlation; measuring the amount of transformation needed for the image mapping; and measuring the residual cost function values before and after the image mapping.

In some embodiments, anatomical features of a patient of interest with respect to the population data in the image-based clinical database may be mapped. Mapping may include the steps of performing unsupervised analysis such as principal component analysis of the structured anatomical information or transformation matrices; and performing supervised analysis, in which the clinical information in the Clinical database is incorporated, such as linear discriminant analysis. The anatomy of the patient may be mapped within the population based on anatomical similarity or similarity in clinically meaningful anatomical features using similarity indices such as distances in the anatomical domains.

In some embodiments, clinically relevant information stored in the Clinical database may be reported, which may include identifying past cases that share similar anatomical features or clinically important anatomical features; summarizing the clinical information in structured or unstructured text fields from the cases that share similar anatomical features or clinically important anatomical features; and using natural language processing methods to extract and summarize relevant clinical information of the structured or unstructured text fields from the cases that share similar anatomical features or clinically important anatomical features.

In some embodiments, a cluster and/or hierarchy may be created within the image data stored in the Clinical database, which may include performing image mapping such as voxel-based image transformation among all pair of data within the database; and performing image structurization using image-vector or image-matrix conversion methods such as image segmentation and parcellation. The voxel-based image transformation may create image transformation matrices that describe anatomical differences and similarities among the cases in the database. The structured data such as vectors and matrices may be used to calculate indices describing the anatomical similarities. Non-image clinical information may be added to the image-based information to calculate similarity among the cases in the database.

Clusters may be created based on the results from the image transformation matrices that describe anatomical differences and similarities among the cases in the database, from the indices describing the anatomical similarities, and from the calculated similarity among the cases in the database. Representing cases may be chosen or created for each cluster. A representing case for each cluster may be calculated using population-averaging tools based on linear or non-linear image transformation. Multiple levels of clusters may be created based on the clustering results. A representative case for each level of a cluster may be chosen or calculated.

In some embodiments, appropriate clusters or representative cases may be chosen to perform image mapping and population mapping to enhance their efficiency and accuracy.

In some embodiments, brain mapping and image parcellation may be performed using an iterative approach, which may include performing initial rough mapping or parcellation using a single-atlas mapping and/or non-cpu-intensive image transformation; using the transformation matrix or structurized anatomical feature matrices to search appropriate cases (atlases) inside the existing Clinical Database; using the cluster representative cases to further enhance the efficiency of the image search; performing single-atlas or multiple-atlas image mapping or parcellation to enhance the mapping or parcellation accuracy; using the improved mapping or parcellation information to search cases (atlases) inside the existing Clinical Database; and, if necessary, performing further searching inside the proper clusters to obtain single or multiple atlases with similar anatomical features, in which the iterative searches may gradually descend the cluster hierarchy to improve the mapping and parcellation accuracy. The iterative descending of hierarchy may achieve improved accuracy for the population mapping, in which past cases with similar anatomical features are identified.

Figure 9:
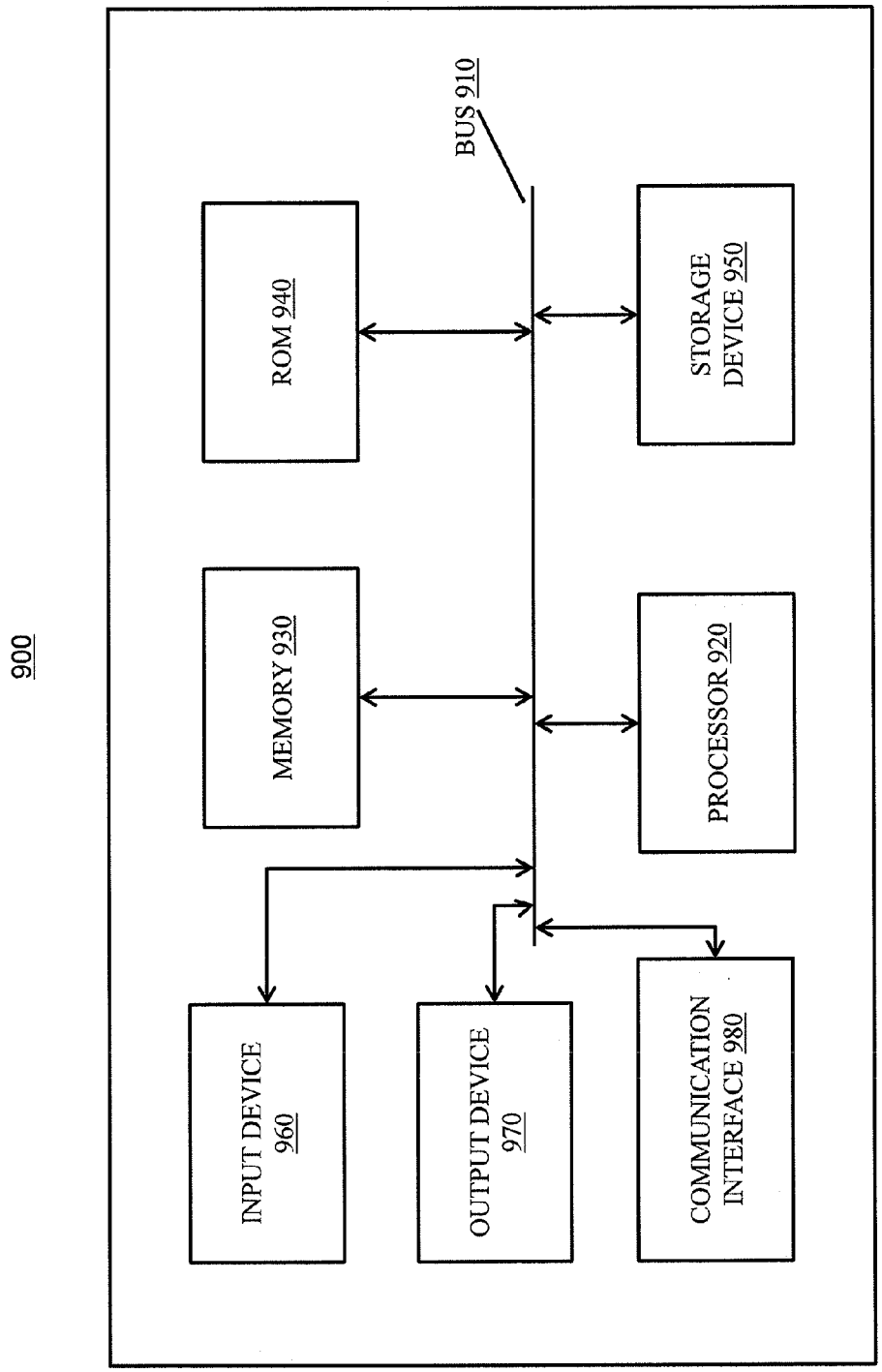
FIG. 9 depicts an exemplary architecture for implementing a computing device in accordance with one or more embodiments.

FIG. 9 depicts an exemplary architecture for implementing a computing device 900 in accordance with one or more embodiments, which may be used to implement the biological imaging grid, or any other computer system or computing device component thereof. It will be appreciated that other devices that can be used with the computing device 900, such as a client or a server, may be similarly configured. As illustrated in FIG. 9, computing device 900 may include a bus 910, a processor 920, a memory 930, a read only memory (ROM) 940, a storage device 950, an input device 960, an output device 970, and a communication interface 980.

Bus 910 may include one or more interconnects that permit communication among the components of computing device 900. Processor 920 may include any type of processor, microprocessor, or processing logic that may interpret and execute instructions (e.g., a field programmable gate array (FPGA)). Processor 920 may include a single device (e.g., a single core) and/or a group of devices (e.g., multi-core). Memory 930 may include a random access memory (RAM) or another type of dynamic storage device that may store information and instructions for execution by processor 920. Memory 930 may also be used to store temporary variables or other intermediate information during execution of instructions by processor 920.

ROM 940 may include a ROM device and/or another type of static storage device that may store static information and instructions for processor 920. Storage device 950 may include a magnetic disk and/or optical disk and its corresponding drive for storing information and/or instructions. Storage device 950 may include a single storage device or multiple storage devices, such as multiple storage devices operating in parallel. Moreover, storage device 950 may reside locally on the computing device 900 and/or may be remote with respect to a server and connected thereto via network and/or another type of connection, such as a dedicated link or channel.

Input device 960 may include any mechanism or combination of mechanisms that permit an operator to input information to computing device 900, such as a keyboard, a mouse, a touch sensitive display device, a microphone, a pen-based pointing device, and/or a biometric input device, such as a voice recognition device and/or a finger print scanning device. Output device 970 may include any mechanism or combination of mechanisms that outputs information to the operator, including a display, a printer, a speaker, etc.

Communication interface 980 may include any transceiver-like mechanism that enables computing device 900 to communicate with other devices and/or systems, such as a client, a server, a license manager, a vendor, etc. For example, communication interface 980 may include one or more interfaces, such as a first interface coupled to a network and/or a second interface coupled to a license manager. Alternatively, communication interface 980 may include other mechanisms (e.g., a wireless interface) for communicating via a network, such as a wireless network. In one implementation, communication interface 980 may include logic to send code to a destination device, such as a target device that can include general purpose hardware (e.g., a personal computer form factor), dedicated hardware (e.g., a digital signal processing (DSP) device adapted to execute a compiled version of a model or a part of a model), etc.

Computing device 900 may perform certain functions in response to processor 920 executing software instructions contained in a computer-readable medium, such as memory 930. In alternative embodiments, hardwired circuitry may be used in place of or in combination with software instructions to implement features consistent with principles of the disclosure. Thus, implementations consistent with principles of the invention are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

It is worthy to note that any reference to "one embodiment" or "an embodiment" means that a particular feature, structure, or characteristic described in connection with the embodiment is included in at least one embodiment. The appearances of the phrase "in one embodiment" in the specification are not necessarily all referring to the same embodiment.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible storage media.

It also is to be appreciated that the described embodiments illustrate exemplary implementations, and that the functional components and/or modules may be implemented in various other ways which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

While various exemplary embodiments have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

The invention claimed is:

1. A computer-implemented method for evidence-based statistical diagnosis support, comprising:
   receiving reference data for a plurality of reference cases represented in a feature space, wherein each reference case of said plurality of reference cases is based at least partially on corresponding imaging data and is associated with non-image clinical information;
   segmenting the imaging data of each said reference case into a plurality of substructures for each of the plurality of reference cases;
   determining an anatomical property associated with each substructure of the imaging data of the plurality of reference cases;
   identifying a point in said feature space for each reference case based on at least said segmenting and said determining said anatomical property;
   receiving data for a subject, said data comprising an input image;
   segmenting the input image into a plurality of substructures;
   determining an anatomical and non-anatomical property associated with each substructure of the plurality of substructures of the input image;
   identifying a point in the feature space corresponding to the data for said subject based at least partially on the anatomical properties determined for said plurality of substructures of said standardized input image;
   selecting a subset of reference cases from said plurality of reference cases based on distances of said point in said feature space corresponding to said data for said subject to each point in said feature space for each reference case; and
   generating subject-specific clinical information based on the subset of reference cases using the corresponding non-image clinical information of each reference case in the subset of reference cases.

2. The method of claim 1, wherein the subset of reference cases further comprises multi-level clusters, and
   wherein selecting said subset of reference cases from said plurality of reference cases is based on distances of said point in said feature space for said subject to at least one of the multi-level clusters.

3. The method of claim 2, wherein the selecting said subset of reference cases from said plurality of reference cases takes place only to one or more reference cases that represent one or more clusters to increase the efficiency of mapping.

4. The method of claim 1, wherein the subset of reference cases and the input image correspond to a same bodily segment.

5. The method of claim 1, wherein generating said subject-specific non-image clinical information based on the subset of reference cases and the corresponding non-image clinical information further comprises:
   identifying non-image clinical information that corresponds to the subset of reference cases; and
   selecting the subject-specific non-image clinical information from the identified non-image clinical information when an amount of the subject-specific non-image clinical information exceeds a threshold.

6. The method of claim 1, wherein the non-image clinical information comprises at least one of demographic information, one or more clinical symptoms, one or more functional test results, one or more diagnoses, and one or more prognoses.

7. The method of claim 1, further comprising:
   presenting the subject-specific non-image clinical information as a report; or
   transmitting the subject-specific non-image clinical information to a recipient.

8. The method of claim 1, further comprising selecting one or more reference cases with higher level of anatomical similarity to increase selecting accuracy.

9. The method of claim 1, wherein the selecting is based on diffeomorphic image transformation.

10. The method of claim 1, further comprising:
standardizing the imaging data of the plurality of reference cases with respect to each other;
standardizing said input image of said subject with respect to said imaging data of the plurality of reference cases to provide a standardized input image,
wherein segmenting segments said standardized input image.

11. The method of claim 10, wherein the anatomical space is an N-dimension anatomical space.

12. The method of claim 11, wherein N is a number that corresponds to the number of segmented substructures.

13. The method of claim 1, wherein said feature space is an anatomical space.

14. A system for evidence-based statistical diagnosis support, comprising:
a memory; and
a processor connected to the memory and configured to:
receive reference data for a plurality of reference cases represented in an feature space, wherein each reference case of said plurality of reference cases is based at least partially on corresponding imaging data and is associated with non-image clinical information;
standardize the imaging data of the plurality of reference cases with respect to each other;
segment the imaging data of each said reference case into a plurality of substructures for each of the plurality of reference cases;
determine an anatomical property associated with each substructure of the imaging data of the plurality of reference cases;
identify a point in said feature space for each reference case based on at least said segmenting and said determining said anatomical property;
receive data for a subject, said data comprising an input image;
standardize said input image of said subject with respect to said imaging data of the plurality of reference cases to provide a standardized input image;
segment the standardized input image into a plurality of substructures;
determine an anatomical property associated with each substructure of the plurality of substructures;
identify a point in the feature space corresponding to the data for said subject based at least partially on the anatomical properties determined for said plurality of substructures of said standardized input image;
select a subset of reference cases from said plurality of reference cases based on distances of said point in said feature space corresponding to said data for said subject to each point in said feature space for each reference case; and
generate subject-specific clinical information based on the subset of reference cases using the corresponding non-image clinical information of each reference case in the subset of reference cases.

15. The system of claim 14, wherein the subset of reference cases further comprise multi-level clusters, and wherein selecting said subset of reference cases from said plurality of reference cases is based on distances of said point in said feature space for said subject to at least one of the multi-level clusters.

16. The system of claim 14, wherein the subset of reference cases and the input image correspond to a same bodily segment.

17. The system of claim 14, wherein the processor is further configured to:
identify non-image clinical information that corresponds to the subset of reference cases; and
select the subject-specific non-image clinical information from the identified non-image clinical information when an amount of the subject-specific non-image clinical information exceeds a threshold.

18. The system of claim 14, wherein the non-image clinical information comprises at least one of demographic information, one or more clinical symptoms, one or more functional test results, one or more diagnoses, and one or more prognoses.

19. The system of claim 14, wherein the processor is further configured to:
present the subject-specific non-image clinical information as a report; or
transmit the subject-specific non-image clinical information to a recipient.

20. A non-transitory computer readable storage medium for evidence-based statistical diagnosis support, the computer readable storage medium comprising instructions that if executed enable a computing system to:
receive reference data for a plurality of reference cases represented in a feature space, wherein each reference case of said plurality of reference cases is based at least partially on corresponding imaging data and is associated with non-image clinical information;
standardize the imaging data of the plurality of reference cases with respect to each other;
standardize said plurality of clinical images of said subjects with respect to said imaging data of the plurality of reference cases to provide a plurality of standardized clinical images;
segment the plurality of standardized clinical images into a plurality of substructures for each image of the plurality of standardized clinical images;
determine an anatomical property associated with each substructure of the imaging data of the plurality of reference cases;
identify a point in said feature space for each reference case based on at least said segmenting and said determining said anatomical property; and
store the plurality of reference cases in a database.

21. The computer readable storage medium of claim 20, further comprising instructions that if executed enable the computing system to:
receive data from a subject, said data comprising an input image;
standardize said input image of said subject with respect to said imaging data of the plurality of reference cases to provide a standardized input image;
segment the standardized input image into a plurality of substructures;
determine an anatomical property associated with each substructure of the plurality of substructures;
identify a point in the feature space corresponding to the data for said subject based at least partially on the anatomical properties determined for said plurality of substructures of said standardized input image;
select a subset of reference cases from said plurality of reference cases based on distances of said point in said feature space corresponding to said data for said subject to each point in said feature space for each reference case; and generate subject-specific non-image clinical information based on the subset of reference cases using the corresponding non-image clinical information of each reference case in the subset of reference cases.

22. The computer readable storage medium of claim 21, wherein the one or more reference cases of the plurality of reference cases further comprise multi-level clusters, and wherein mapping the input image to the one or more reference cases of the plurality of reference cases using the second plurality of anatomical properties further comprises instructions that if executed enable the computing system to:

map the input image to at least one of the multi-level clusters.

23. The computer readable storage medium of claim 21, wherein the subset of reference cases and the input image correspond to a same bodily segment.

24. The computer readable storage medium of claim 21, wherein generating said subject-specific non-image clinical information based on the subset of reference cases and the corresponding non-image clinical information further comprises instructions that if executed enable the computing system to:

identify non-image clinical information that corresponds to the subset of reference cases; and select the subject-specific non-image clinical information from the identified non-image clinical information when an amount of the identified non-image clinical information exceeds a threshold.

25. The computer readable storage medium of claim 20, wherein said non-image clinical information comprises at least one of demographic information, one or more clinical symptoms, one or more functional test results, one or more diagnoses, and one or more prognoses.

26. The computer readable storage medium of claim 21, further comprising instructions that if executed enable the computing system to:

present the subject-specific non-image clinical information as a report; or transmit the subject-specific non-image clinical information to a recipient.

27. A computer-implemented method comprising:

mapping anatomical features of a patient of interest with respect to population data in a feature space from an image-based clinical database;

performing unsupervised analysis of the anatomical features of said patient using structured anatomical information matrices of the population data; and performing supervised analysis of the anatomical features of said patient, wherein clinical information in the image-based clinical database is incorporated.

28. The method of claim 27, wherein an anatomy of the patient is mapped within a population based on anatomical similarity or similarity in clinically meaningful anatomical features using similarity indices.

29. A computer-implemented method comprising:

identifying a point in a feature space for each of image data stored in a clinical database;

determining distances among pairs of data in the features space from the image data stored in the database;

performing image structurization using image-vector or image-matrix conversion methods to produce anatomical image feature vectors or anatomical image feature matrices; and based on the image feature vectors or image feature matrices, calculating a plurality of clusters based on similarity among the image feature vectors or image feature matrices.

30. The method of claim 29, wherein a representing case for each cluster is randomly selected within the cluster or calculated using population-averaging tools based on linear or non-linear image transformation.

31. A computer-implemented method to perform brain mapping and image parcellation using an iterative approach comprising:

identifying a point in a feature space for each of image data stored in a clinical database;

determining distances among pairs of data in the feature space from the image data stored in the database;

performing image structurization using image-vector or image-matrix conversion methods to produce anatomical image feature vectors or anatomical image feature matrices;

using the anatomical image feature vectors or anatomical image feature matrices to search similar references;

calculating a plurality of clusters based on similarity among the image feature vectors or image feature matrices;

if necessary, further searching inside proper clusters to obtain single or multiple references with similar anatomical features; and iteratively searching by descending a cluster hierarchy to improve the mapping and parcellation accuracy.

32. The method of claim 31, wherein the iterative descending of a cluster hierarchy achieves improved accuracy for the population mapping by identifying similar anatomical features.

* * * * *

UNITED STATES PATENT AND TRADEMARK OFFICE
CERTIFICATE OF CORRECTION

| | | |
|---|---|---|
| PATENT NO. | : 9,646,138 B2 | Page 1 of 1 |
| APPLICATION NO. | : 14/367593 | |
| DATED | : May 9, 2017 | |
| INVENTOR(S) | : Mori et al. | |

It is certified that error appears in the above-identified patent and that said Letters Patent is hereby corrected as shown below:

In the Specification

Column 1, Lines 12-15 replace with the following paragraph:
This invention was made with government support under R01AG020012 and P41EB015909 awarded by the National Institutes of Health. The government has certain rights in the invention.

Signed and Sealed this
Fifth Day of December, 2017

Joseph Matal
*Performing the Functions and Duties of the*
*Under Secretary of Commerce for Intellectual Property and*
*Director of the United States Patent and Trademark Office*